US008542891B2

(12) United States Patent
Yokota et al.

(10) Patent No.: US 8,542,891 B2
(45) Date of Patent: Sep. 24, 2013

(54) X-RAY IMAGING APPARATUS THAT DISPLAYS ANALYSIS IMAGE WITH TAKEN IMAGE, X-RAY IMAGING METHOD, AND IMAGE PROCESSING APPARATUS

(75) Inventors: Tetsuya Yokota, Otawara (JP); Hitoshi Yamagata, Otawara (JP); Satoshi Wakai, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 1014 days.

(21) Appl. No.: 12/486,096

(22) Filed: Jun. 17, 2009

(65) Prior Publication Data

US 2010/0002839 A1    Jan. 7, 2010

(30) Foreign Application Priority Data

Jul. 4, 2008    (JP) ................................ 2008-176042

(51) Int. Cl.
*G06K 9/00*    (2006.01)
(52) U.S. Cl.
USPC ........... 382/128; 382/130; 382/132; 382/294; 378/98.2; 378/98.11; 378/98.12
(58) Field of Classification Search
None
See application file for complete search history.

(56) References Cited

U.S. PATENT DOCUMENTS

| 7,369,691 | B2 | 5/2008 | Kondo et al. | |
| 7,519,414 | B2 | 4/2009 | Mitschke et al. | |
| 7,697,740 | B2 * | 4/2010 | Fujisawa | 382/128 |
| 2005/0054916 | A1 * | 3/2005 | Mostafavi | 600/427 |
| 2006/0262970 | A1 * | 11/2006 | Boese et al. | 382/131 |
| 2007/0003016 | A1 * | 1/2007 | Brunner et al. | 378/98.12 |
| 2007/0092067 | A1 * | 4/2007 | Fujisawa | 378/196 |

FOREIGN PATENT DOCUMENTS

| JP | 06-178771 A | 6/1994 |
| JP | 2004-283373 A | 10/2004 |
| JP | 2006-110344 A | 4/2006 |
| JP | 2007-136164 A | 6/2007 |
| JP | 2007-180761 A | 7/2007 |
| JP | 2007-282945 A | 11/2007 |
| JP | 2008-012171 A | 1/2008 |
| JP | 2009-034494 A | 2/2009 |

OTHER PUBLICATIONS

Japanese Office Action with English Translation for Japanese Patent Application No. 2009-109409 mailed on May 21, 2013.

* cited by examiner

*Primary Examiner* — Matthew Bella
*Assistant Examiner* — Jason Heidemann
(74) *Attorney, Agent, or Firm* — Yoshida & Associates, LLC

(57) ABSTRACT

Positioning images are created by a projection-image creating unit before imaging, and the positioning images are grouped and stored by a projection-image storage unit for each preset. When imaging is started, a positioning-information calculating unit calculates positioning parameters using the positioning images stored in the projection-image storage unit. An analysis-image-for-synthesis creating unit creates an analysis image using the positioning parameters, and an analysis-image synthesizing and displaying unit synthesizes the analysis image with a live image and displays a synthesized image. When an imaging direction of an X-ray angiography apparatus is changed, a positioning-information updating unit directly updates the positioning parameters based on an amount of change of the imaging direction.

18 Claims, 12 Drawing Sheets

FIG.2
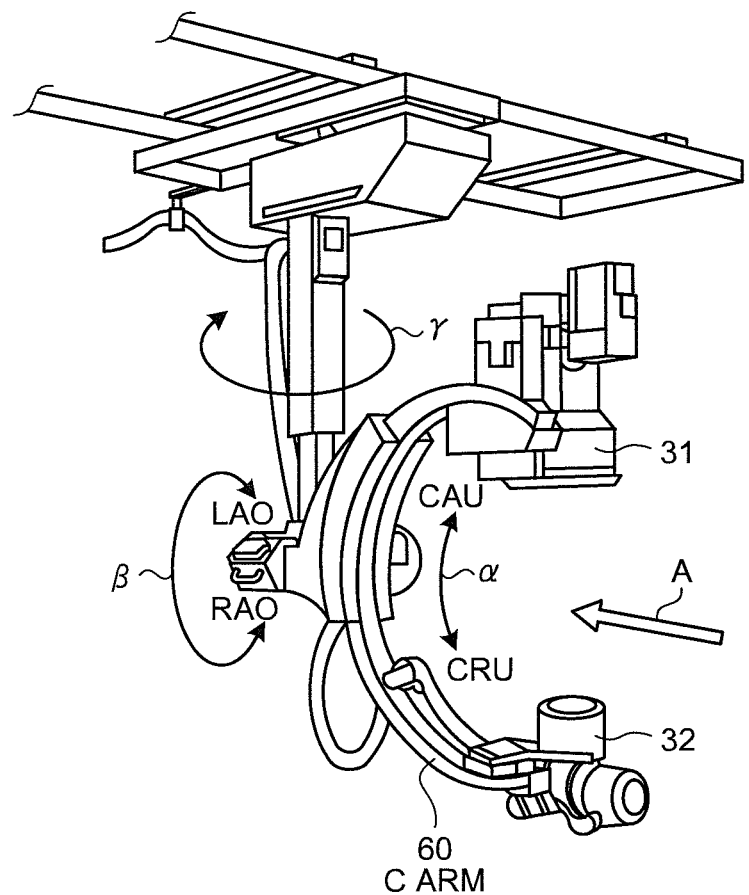
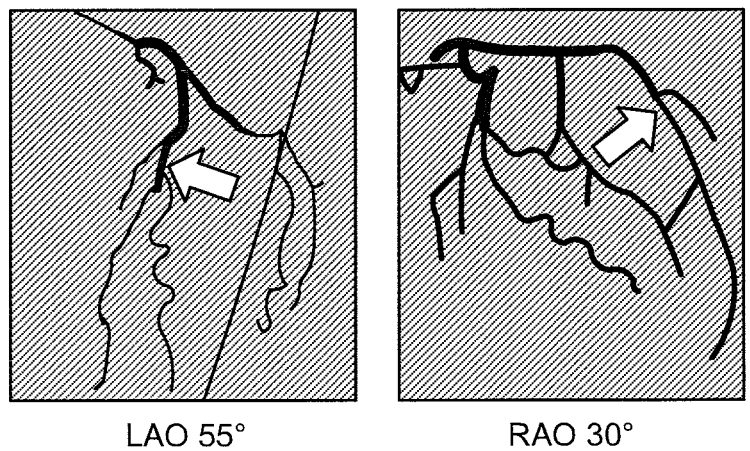
LAO 55°    RAO 30°

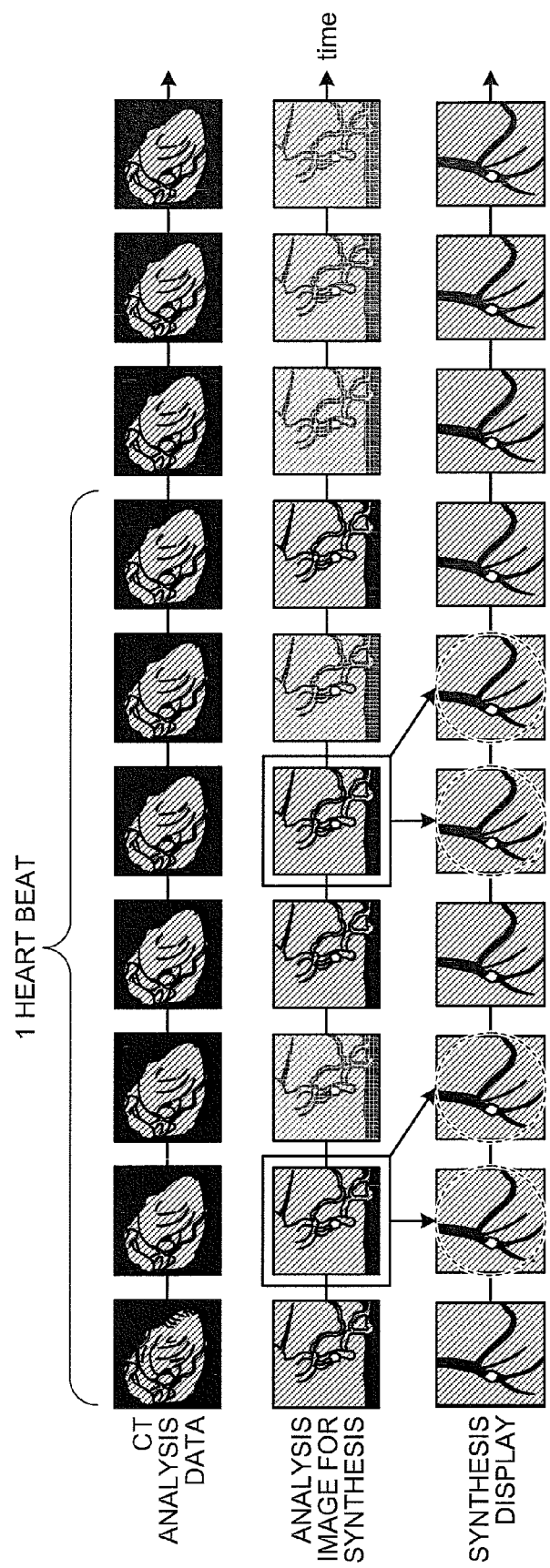

X-RAY IMAGING APPARATUS THAT DISPLAYS ANALYSIS IMAGE WITH TAKEN IMAGE, X-RAY IMAGING METHOD, AND IMAGE PROCESSING APPARATUS

CROSS-REFERENCE TO RELATED APPLICATIONS

This application is based upon and claims the benefit of priority from the prior Japanese Patent Application No. 2008-176042, filed on Jul. 4, 2008; the entire contents of which are incorporated herein by reference.

BACKGROUND OF THE INVENTION

1. Field of the Invention

The present invention relates to a technique of displaying an analysis image of a target region such as an angiostenosis part with an X-ray image being taken.

2. Description of the Related Art

Conventionally, there has been a treatment technique such that a linear structure such as a guide wire or a catheter is inserted into coronary arteries of a heart to expand a portion where the coronary arteries are narrow or blocked. This treatment technique is referred to as "Percutaneous Coronary Intervention (PCI) treatment". In the PCI treatment, an X-ray imaging apparatus such as an X-ray angiography apparatus is used. The X-ray angiography apparatus displays an X-ray perspective projection image (hereinafter, "X-ray angiographic image") as a guide image at the time of inserting a guide wire up to a lesioned part (a coronary artery stenosis site) during the PCI treatment.

Further, as means for diagnosing coronary arteries, clinical application software for an X-ray CT scanner referred to as "coronary artery analysis software" has been known (for example, see JP-A 2004-283373 (KOKAI)). This coronary artery analysis software has a function for obtaining a blood vessel core of the coronary arteries, an internal wall of a blood vessel, an estimated normal internal wall of a blood vessel, and the like as three-dimensional data using three-dimensional volume data of a heart area.

In PCI treatment, therefore, images of the internal wall of a blood vessel obtained by the coronary artery analysis software are displayed on an another apparatus separate from an X-ray angiography apparatus or developed on a film for reference, to support an operator.

Further, a technique for synthesizing and displaying analysis images showing an angiostenosis part and a running direction of a blood vessel obtained by coronary artery analysis software on an X-ray angiographic image has been developed. To generate the analysis images of the angiostenosis part and the running direction of a blood vessel, projection parameters (projection directions, positions, and enlargement ratios) need to be obtained. To obtain these projection parameters, therefore, a positioning process is performed in a following procedure.

(1) First, to match a projection direction, a user manually sets so that a projection direction of volume data becomes the same as that of the X-ray angiography apparatus.

(2) The volume data is projected from the direction set in procedure (1) to generate an MIP image, and the maximum intensity projection (MIP) image is binarized to an imaged blood area and other areas.

(3) An image showing only the blood area imaged by binarization is generated from the X-ray angiographic image.

(4) To perform positioning between binarized image f1(x, y) in procedure (2) and binarized image f2(x, y) in procedure (3), a parallel shifting amount (l, m) and an expansion ratio s are obtained by a correlation function shown in an equation (1).

$$r(l, m, s) = \frac{1}{N^2} \sum_{x=-N/2}^{N/2-1} \sum_{y=-N/2}^{N/2-1} f_1(x, y) \cdot f_2((x+l)/s, (y+m)/s) \quad (1)$$

However, in the positioning process mentioned above, entire processing is performed after imaging by the X-ray angiography apparatus has started, and thus a longer processing time is required. During PCI treatment, an operator performs surgery, while appropriately changing the imaging direction and position of the X-ray angiography apparatus so that an observation target can be clearly seen on the displayed image. Therefore, every time the imaging direction of the X-ray angiography apparatus is changed, the positioning process needs to be performed from procedure (1), and thus the waiting time for positioning is required. As a result, the surgery time becomes longer, and strains on the patient increase.

SUMMARY OF THE INVENTION

According to one aspect of the present invention, an X-ray imaging apparatus includes an imaging unit that irradiates X-rays on a subject and detects X-rays penetrating the subject to generate an X-ray projection image of the subject; a positioning-image creating unit that creates positioning images corresponding to a plurality of different projection conditions using volume data collected from the subject by a medical imaging apparatus; a projection-condition obtaining unit that selects an image most analogous to the X-ray projection image of the subject from the positioning images, and obtains a projection condition of the selected positioning image; a target-region storage unit that stores volume data of a target region, among the volume data collected, as target-region volume data; and an image display unit that creates and displays an image of the target region based on the target-region volume data stored in the target-region storage unit and the projection condition obtained by the projection-condition obtaining unit.

According to another aspect of the present invention, an X-ray imaging method includes irradiating X-rays on a subject; detecting X-rays penetrating the subject; generating an X-ray projection image of the subject; creating positioning images corresponding to a plurality of different projection conditions using volume data collected from the subject by a medical imaging apparatus; selecting an image most analogous to the X-ray projection image of the subject from the positioning images; obtaining a projection condition of the selected positioning image; storing volume data of a target region, among the volume data collected, as target-region volume data; and creating and displaying an image of the target region based on the target-region volume data and the projection condition.

According to still another aspect of the present invention, an image processing apparatus includes an image obtaining unit that obtains an X-ray projection image of a subject; a positioning-image creating unit that creates positioning images corresponding to a plurality of different projection conditions using volume data collected from the subject by a medical imaging apparatus; a projection-condition obtaining unit that selects an image most analogous to the X-ray projection image of the subject from the positioning images, and obtains a projection condition of the selected positioning image; a target-region storage unit that stores volume data of a target region, among the volume data collected, as target-region volume data; and an image display unit that creates and displays an image of the target region based on the target-region volume data stored in the target-region storage unit and the projection condition obtained by the projection-condition obtaining unit.

BRIEF DESCRIPTION OF THE DRAWINGS

FIG. 2 is a diagram illustrating examples of presets;

FIG. 15 is a diagram illustrating display examples of synthesized images.

DETAILED DESCRIPTION OF THE PREFERRED EMBODIMENTS

Exemplary embodiments of an X-ray imaging apparatus, an X-ray imaging method, and an image processing apparatus according to the present invention will be explained below in detail with reference to the accompanying drawings.

Figure 1:
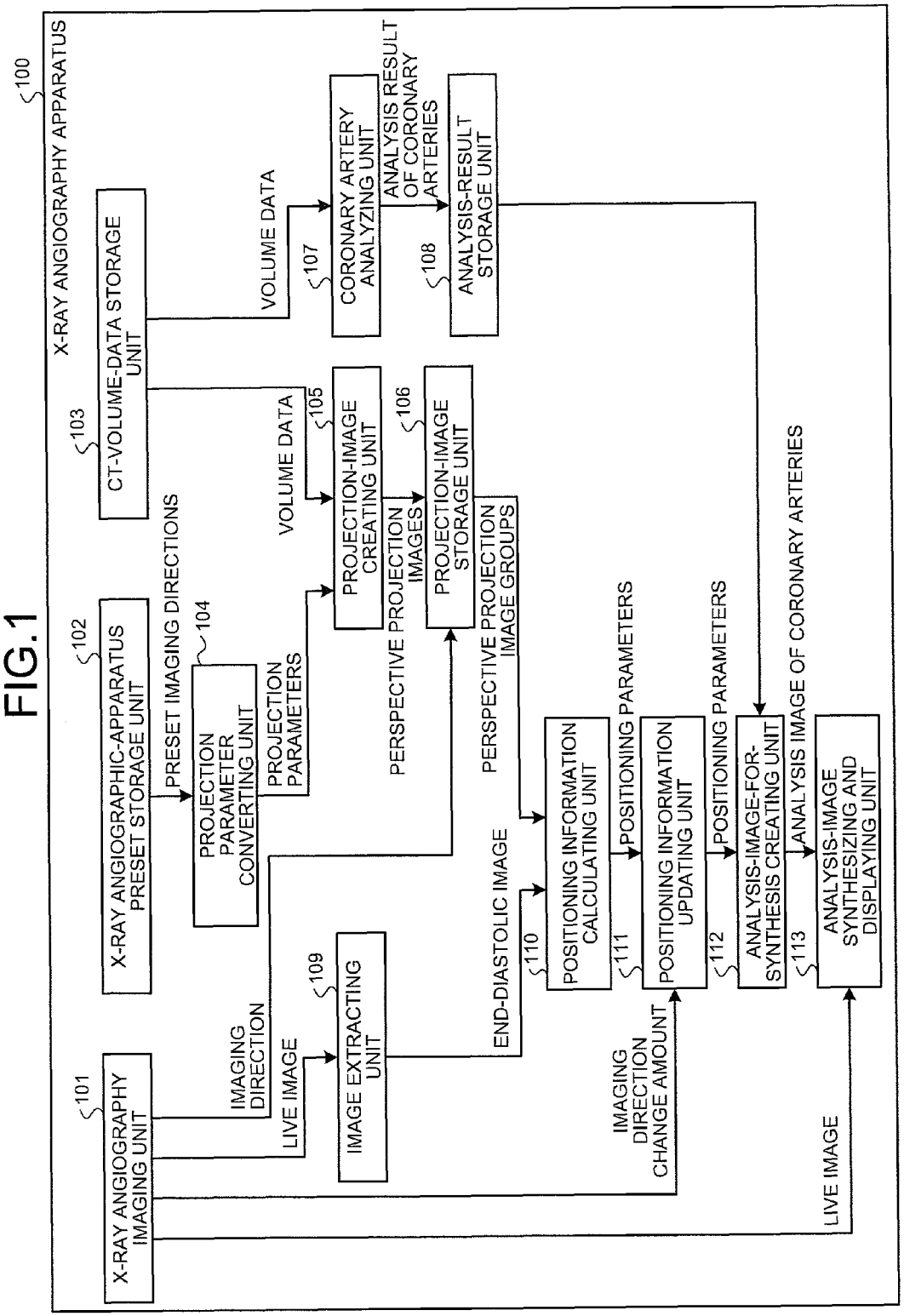
FIG. 1 is a functional block diagram of a configuration of an X-ray angiography apparatus according to a first embodiment of the present invention.

A configuration of an X-ray angiography apparatus according to a first embodiment of the present invention is explained first. FIG. 1 is a functional block diagram of the configuration of the X-ray angiography apparatus according to the first embodiment. As shown in FIG. 1, an X-ray angiography apparatus 100 includes an X-ray angiography imaging unit 101, an X-ray angiographic-apparatus preset storage unit 102, a CT-volume-data storage unit 103, a projection parameter converting unit 104, a projection-image creating unit 105, a projection-image storage unit 106, a coronary artery analyzing unit 107, an analysis-result storage unit 108, an image extracting unit 109, a positioning information calculating unit 110, a positioning-information updating unit 111, an analysis-image-for-synthesis creating unit 112, and an analysis-image synthesizing and displaying unit 113.

The X-ray angiography imaging unit 101 irradiates X-rays on a patient and detects the X-rays having penetrated the patient to generate images. The X-ray angiographic-apparatus preset storage unit 102 stores preset information of the X-ray angiography apparatus 100. As shown in FIG. 2, a plurality of values are registered as preset information, for caudal view (CAU), cranial view (CRA), left anterior oblique view (LAO), and right anterior oblique view (RAO). However, only imaging directions having possibility to be used as an imaging direction at the time of starting treatment are stored in the X-ray angiographic-apparatus preset storage unit 102.

The CAU, CRA, LAO, and RAO represent rotation directions of an isocenter, which is a center of rotation of X-ray beams. In the X-ray angiography apparatus 100, patient's head is made to enter from a direction of arrow "A" (this angle is designated as 0 degree in $\gamma$ angle in FIG. 2), and the apparatus can be rotated in an $\alpha$ direction and a $\beta$ direction, with the $\gamma$ angle being fixed. That is, the X-ray angiography apparatus 100 can be moved in the CRA and CAU directions of the patient by sliding and rotating a C arm 60 that supports an X-ray tube 31 and an X-ray detector 32 in the $\alpha$ direction, and can be moved in the LAO and RAO directions by rotating the C arm 60 in the $\beta$ direction.

The CT-volume-data storage unit 103 stores three-dimensional volume data of a heart area collected by taking images of the patient by an X-ray CT scanner. End-diastolic volume data are used here.

Figure 3:
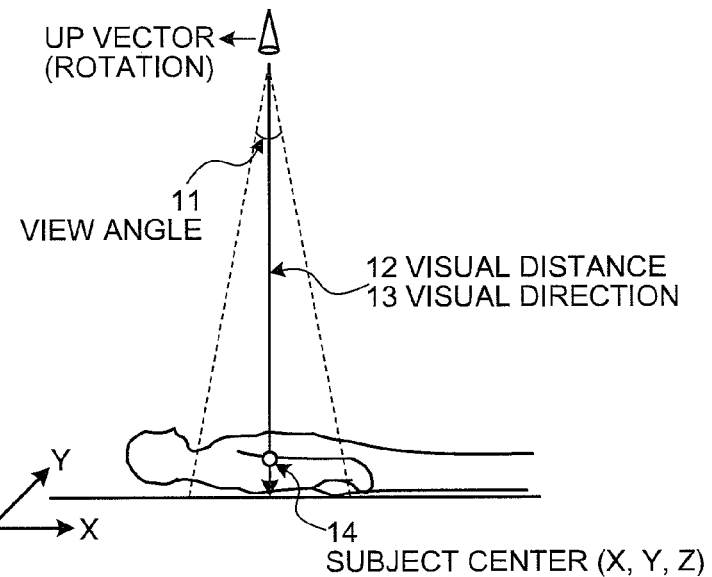
FIG. 3 is a diagram illustrating projection parameters.

The projection parameter converting unit 104 obtains the preset information from the X-ray angiographic-apparatus preset storage unit 102 and converts the preset information to projection parameters. The projection parameters are required for creating a projection image from the volume data, and include a view angle 11, a visual distance 12, a visual direction 13, and a subject center (X, Y, Z) 14 as shown in FIG. 3. The subject center 14 is a central position of X-ray photography, and the view angle 11 expresses a range of the X-ray photography by an angle centering on a focal point of the X-ray tube 31. The visual distance 12 is a distance from the focal point of the X-ray tube 31 to the subject center 14, and the visual direction 13 expresses a direction from the focal point of the X-ray tube 31 to the subject center 14. An Up vector is a rotation angle of the X-ray tube 31.

The view angle, the visual distance, and the visual direction can be converted from the preset information. However, because the subject center depends on an individual difference of physical constitution of the patient and a position of the patient on a bed, the subject center cannot be uniquely determined. Therefore, the projection parameter converting unit 104 obtains initial values of the subject center, for example, according to the following method.

(1) The position on a bed and a patient model are defined on the bed of the X-ray angiography apparatus.

(2) The positions of shoulders in the patient model and the volume data are matched with each other in an anteroposterior direction by referring to a region in which a direction of the patient can be easily specified, such as a collarbone and vertebra.

(3) Correction values are obtained from height and weight of the patient to obtain a deviation of a heart position between the patient model and the volume data.

If the initial values are obtained by this method, a plurality of examples need to be photographed beforehand for the patient model and the correction values.

The projection-image creating unit 105 creates perspective projection images with the subject center being changed within a certain range, from heart area volume data stored in the CT-volume-data storage unit 103, centering on the initial values obtained for the subject center by the projection parameter converting unit 104. The created perspective projection images are grouped for each preset, and stored in the projection-image storage unit 106 in association with the projection parameters.

Figure 4:
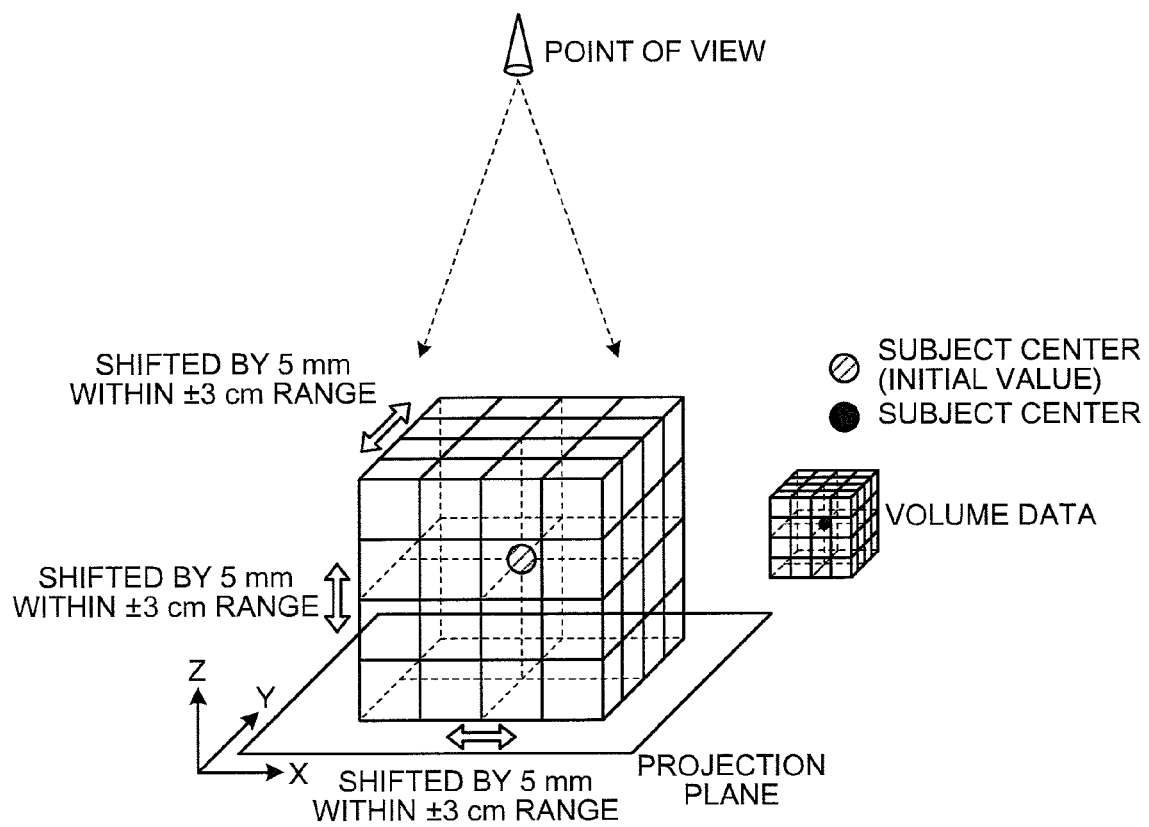
FIG. 4 is a diagram illustrating an example of a range in which a subject center is changed when perspective projection images are created.

The range in which the subject center is changed is, for example, under a condition that the point of view and projection plane shown in FIG. 4 are fixed, ±3 centimeters centering on the initial values of the subject center and with 5 millimeter interval, and 13×13×13 perspective projection images are created. For projection, Ray-Summing (hereinafter, "Ray-Sum") is used, where an integral value of values present on a projection line is designated as a pixel value.

The range for creating the perspective projection images is not limited to this example, and the type of the perspective projection images is not limited to the RaySum, and can be changed according to a comparison method of images used by the positioning information calculating unit 110 described later. The perspective projection images for positioning are created here by changing the subject center. However, the perspective projection images for positioning can be created by changing the Up vector as well, for example, in a case that the shoulder positions are not matched with each other between the patient model and the volume data in the antero-posterior direction. The Up vector is changed, for example, in a range of ±5 degrees and with ±1 degree interval. Further, the perspective projection images for positioning can be created by changing the visual direction. Further, end-diastolic heart phase data are used here as the heart area volume data to be input.

The projection-image storage unit 106 groups and stores the perspective projection images created by the projection-image creating unit 105 for each preset in association with the projection parameters. When the X-ray angiography is started, the projection-image storage unit 106 sets a group corresponding to a preset imaging direction as an image group for positioning.

The coronary artery analyzing unit 107 performs coronary artery analysis to extract volume data of the angiostenosis part from the heart area volume data, and stores the extracted volume data in the analysis-result storage unit 108 as an analysis result. For example, a method described in Japanese Patent Application No. 2007-180761 can be used for the coronary artery analysis. The analysis-result storage unit 108 stores the analysis result, that is, the volume data of the angiostenosis part.

The image extracting unit 109 extracts the heart phase same as that of the heart area volume data, that is, an end-diastolic image from the X-ray angiographic images taken from the preset imaging direction.

The positioning information calculating unit 110 compares the X-ray angiographic image extracted by the image extracting unit 109 with each perspective projection image in the image group set for positioning by the projection-image storage unit 106, thereby searching for a perspective projection image whose position is matched best. The positioning information calculating unit 110 then sets projection parameters corresponding to the perspective projection image whose position is matched best as optimum positioning parameters.

Figure 5:
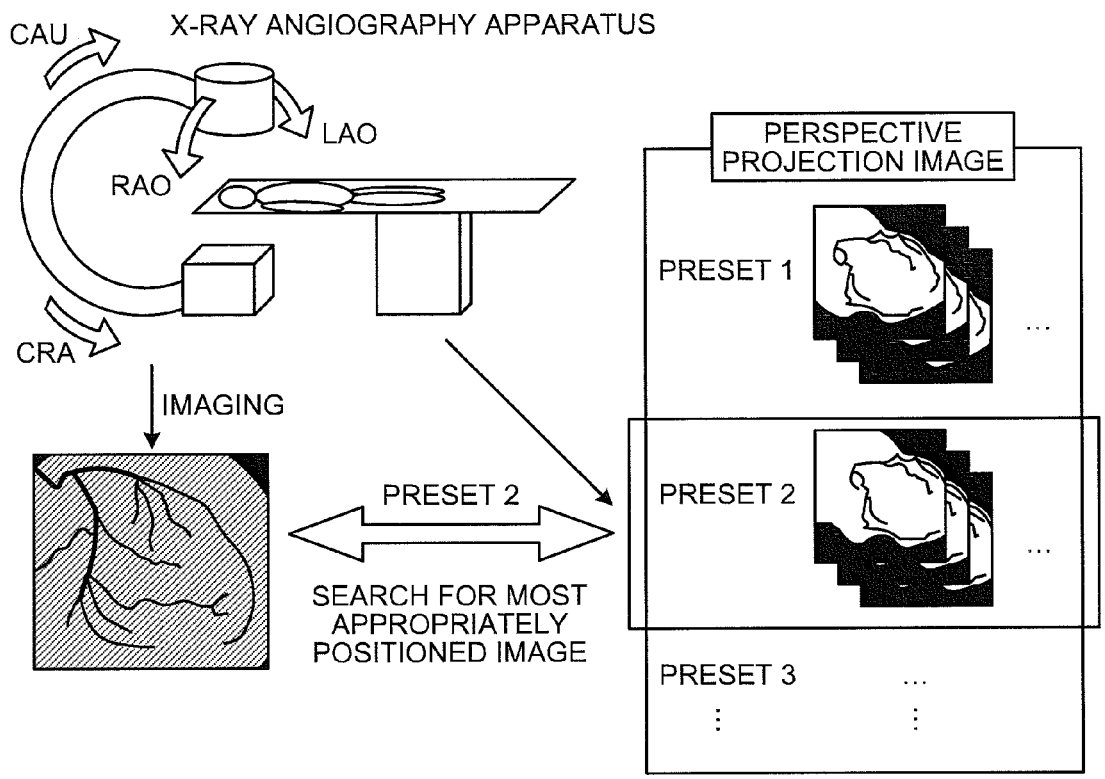
FIG. 5 is a diagram illustrating a search example of a perspective projection image by a positioning information calculating unit.

FIG. 5 is a diagram illustrating a search example of the perspective projection image by the positioning information calculating unit 110. FIG. 5 depicts a case that the preset imaging direction of the X-ray angiography apparatus 100 is "preset 2" and the perspective projection images of an image group of "preset 2" are searched images.

Figure 6:
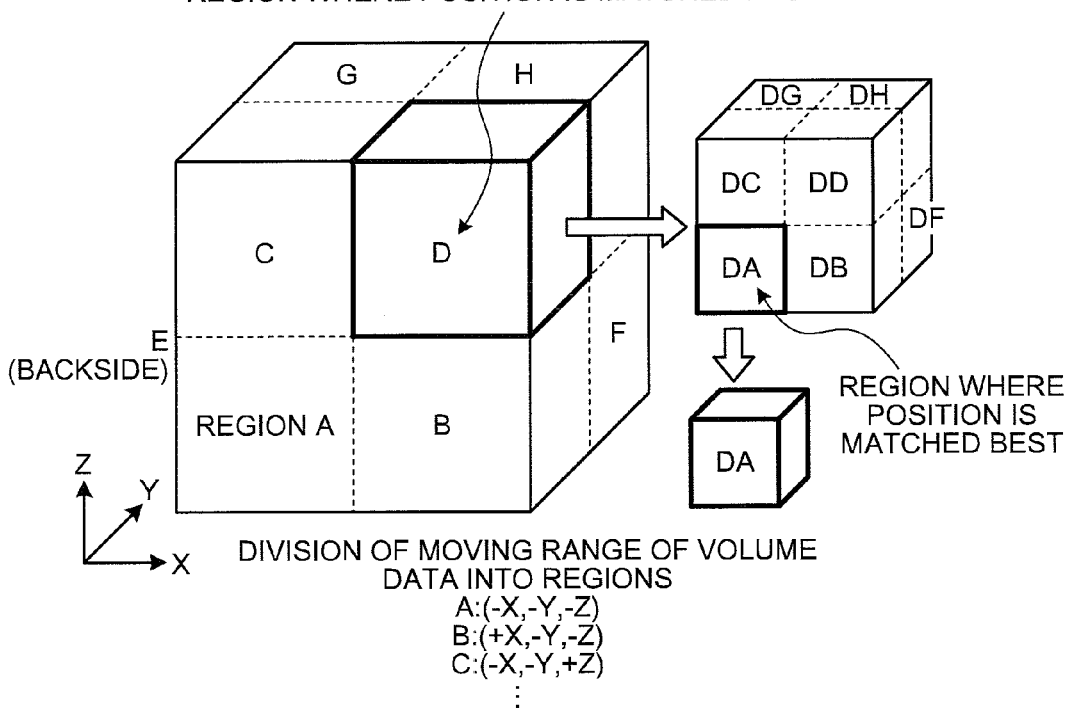
FIG. 6 is a diagram illustrating an example of a method of performing a search while narrowing a comparison range by dividing a region of an image group for positioning into smaller regions.

An image search method includes a method of full-searching the image group for positioning, and a method of performing a search while narrowing a comparison range by dividing a region of an image group for positioning into smaller regions based on an amount of change of the projection parameters. The latter method can perform a search at a higher speed. FIG. 6 is a diagram illustrating an example of the method of performing a search while narrowing the comparison range by dividing a region of an image group for positioning into smaller regions. In this example, a search is performed according to a following procedure.

(1) The perspective projection images are divided into images in regions A to H for each moving direction of the volume data, centering on the initial values of the subject center.

(2) A perspective projection image corresponding to the center of each region is compared with the X-ray angiographic image.

(3) It is assumed that an image whose position is accurate is present in a region including an image whose position is closest to the X-ray angiographic image, and the region is further divided (DA to DH).

(4) Procedures (2) and (3) are repeated, the search region is narrowed, and a full search is performed in a target region.

In this method, by dividing into regions overlapped on each other, selection of a region can be performed without error even if the image whose position is matched best is present near a boundary of the divided regions.

The correlation function shown in the equation (1) or mutual information I shown in an equation (2) below can be used for comparison of the images. In the equation (2), A and B are images, a and b are respectively a pixel in images A and B, P(A) and P(B) are respectively an entropy of the images A and B, P(A,B) is a total entropy, and p(a), p(b), and p(a, b) are probability distribution functions.

$$I(A, B) = P(A) + P(B) - P(A, B) \quad (2)$$

$$= -\sum_a \sum_b p(a, b) \log \frac{p(a, b)}{p(a) + p(b)}$$

The positioning-information updating unit 111 obtains amounts of changes of positioning parameters from a change amount of the imaging direction to update the positioning parameters, when the imaging direction of the X-ray angiography apparatus 100 is changed after setting of the positioning parameters.

The analysis-image-for-synthesis creating unit 112 creates a two-dimensional projection source image of the angiostenosis part as an analysis image for synthesis, using the volume data of the angiostenosis part stored in the analysis-result storage unit 108 and the positioning parameters.

Figure 7:
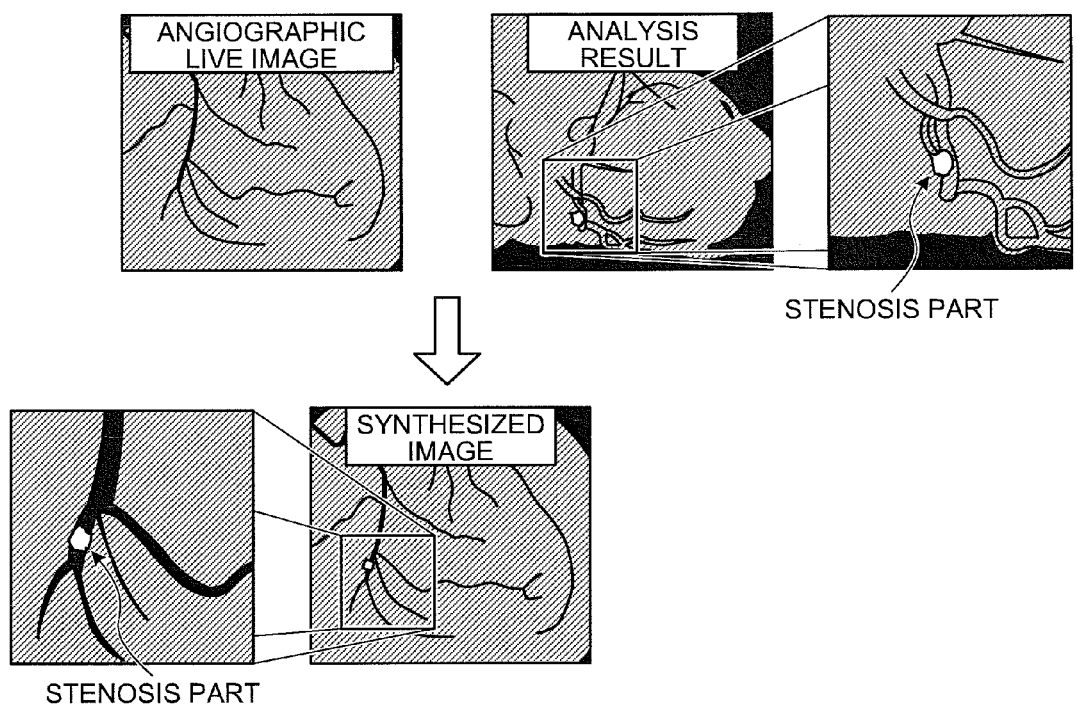
FIG. 7 is a diagram illustrating an example of a synthesized image.

The analysis-image synthesizing and displaying unit 113 synthesizes an image by overlapping the analysis image for synthesis created by the analysis-image-for-synthesis creating unit 112 on the X-ray angiographic image and displays the synthesized image. FIG. 7 is a diagram illustrating an example of a synthesized image.

Figure 8:
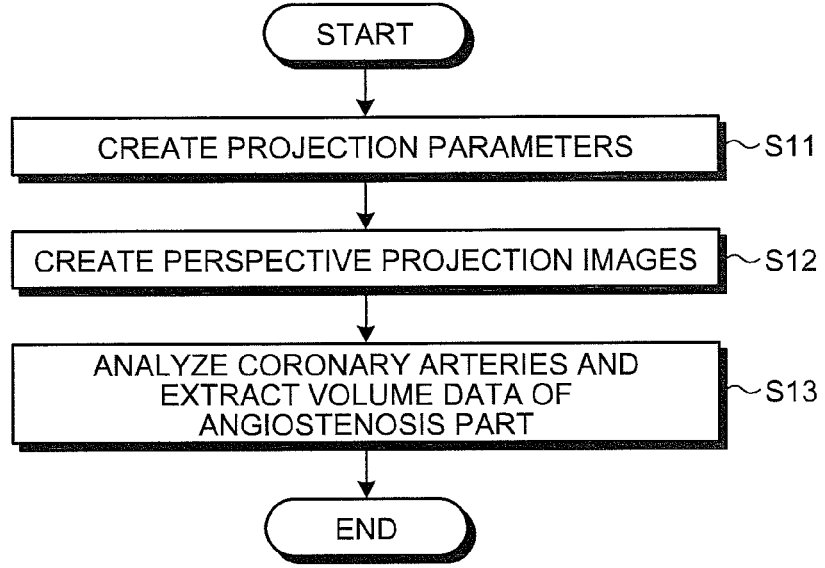
FIG. 8 is a flowchart of a procedure performed by an X-ray angiography apparatus before imaging.

Procedures performed by the X-ray angiography apparatus 100 before imaging and after start of imaging in order to display the synthesized image are explained next with reference to FIGS. 8 and 9. FIG. 8 is a flowchart of the procedure performed by the X-ray angiography apparatus 100 before imaging. As shown in FIG. 8, the projection parameter converting unit 104 obtains preset information from the X-ray angiographic-apparatus preset storage unit 102, to create projection parameters for each preset (Step S11).

The projection-image creating unit 105 creates perspective projection images while changing the subject center for each projection parameter (Step S12), groups the perspective projection images for each preset, and stores the perspective projection images with the projection parameters in the projection-image storage unit 106.

The coronary artery analyzing unit 107 analyzes the heart area volume data to detect an angiostenosis part, and stores the volume data of the angiostenosis part in the analysis-result storage unit 108 (Step S13).

In this way, the projection-image creating unit 105 creates the perspective projection images while changing the subject center for each projection parameter, and stores the perspective projection images with the projection parameters in the projection-image storage unit 106, thereby enabling to perform a positioning process at a high speed after imaging has been started.

Figure 9:
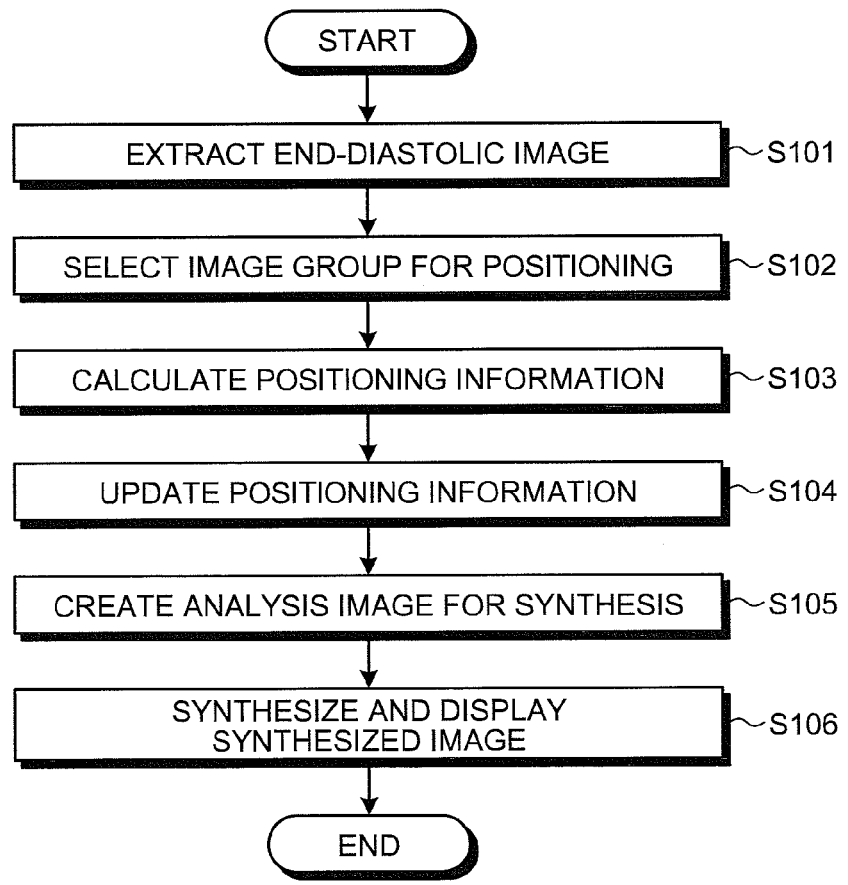
FIG. 9 is a flowchart of a procedure performed by the X-ray angiography apparatus after start of imaging.

FIG. 9 is a flowchart of the procedure performed by the X-ray angiography apparatus 100 after start of imaging. As shown in FIG. 9, when imaging is started, the image extracting unit 109 extracts an end-diastolic image (Step S101), and the projection-image storage unit 106 sets an image group corresponding to a preset imaging direction as an image group for positioning (Step S102).

The positioning information calculating unit 110 then compares the image extracted by the image extracting unit 109 with respective perspective projection images in the image group for positioning, to calculate positioning information, that is, positioning parameters (Step S103). Thereafter, when the imaging direction is changed, the positioning-information updating unit 111 updates the positioning parameters (Step S104).

The analysis-image-for-synthesis creating unit 112 creates an analysis image of the angiostenosis part using the positioning parameters and the volume data stored in the analysis-result storage unit 108 as an image for synthesis (Step S105), and the analysis-image synthesizing and displaying unit 113 overlaps the analysis image of the angiostenosis part on a live image and displays the live image overlapped by the analysis image (Step S106).

As described above, in the first embodiment, the projection-image creating unit 105 creates positioning images before imaging, and the projection-image storage unit 106 groups the positioning images for each preset and stores the images. When imaging is started, the positioning information calculating unit 110 calculates the positioning parameters, using the positioning images stored in the projection-image storage unit 106. Therefore, positioning can be performed at a high speed during imaging, and a synthesized image can be displayed on a real-time basis.

Furthermore, in the first embodiment, when the imaging direction of the X-ray angiography apparatus 100 is changed, the positioning-information updating unit 111 updates the positioning parameters directly based on the change amount of the imaging direction. Accordingly, when the imaging direction of the X-ray angiography apparatus 100 is changed, synthesis and display can be performed on a real-time basis.

As a result, the coronary artery analysis information such as the running direction of the blood vessel and the angiostenosis part can be confirmed on the X-ray angiographic image. Accordingly, confirmation of an advancing direction at the time of inserting a catheter and position adjustment of a treatment tool such as a balloon or a stent can be easily performed, thereby enabling to reduce the operation time. Further, it leads to reduction of usage of a contrast agent and exposure, thereby enabling to reduce strains on the patient.

In the first embodiment, a case that the image for synthesis of the angiostenosis part is created, and displayed, overlapped on the live image has been explained. However, not only the angiostenosis part but also an analysis image for synthesis expressing other target regions and noteworthy information in the PCI treatment such as a running direction of a blood vessel, a blood flow rate, plaque characteristics, and a rate of stenosis can be overlapped on the live image and displayed. In a second embodiment of the present invention, therefore, an X-ray angiography apparatus that selectively overlaps an analysis image for synthesis relating to a plurality of target regions and the noteworthy information on the live image and displays the live image overlapped by the analysis image is explained.

Figure 10:
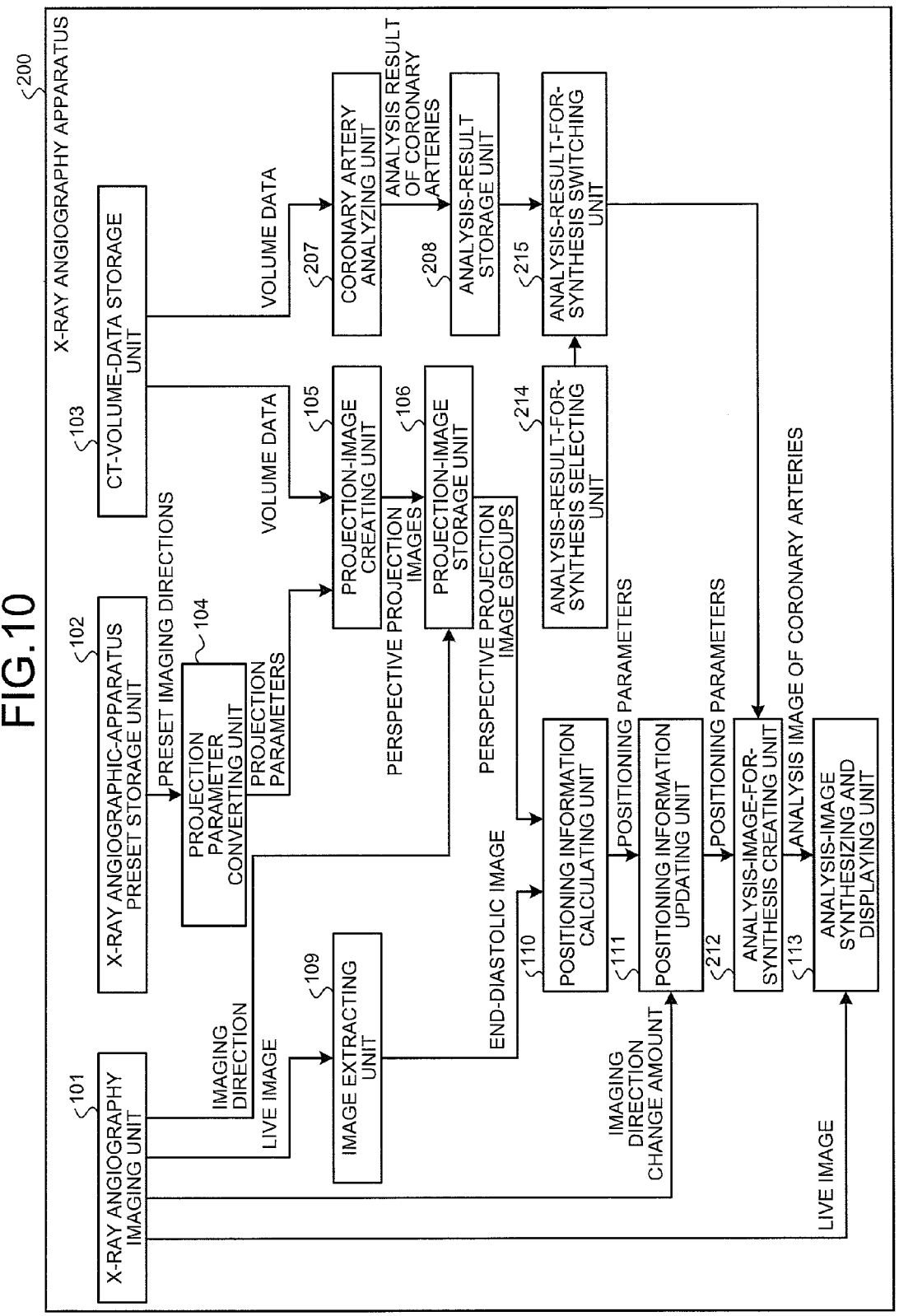
FIG. 10 is a functional block diagram of a configuration of an X-ray angiography apparatus according to a second embodiment of the present invention.

FIG. 10 is a functional block diagram of a configuration of an X-ray angiography apparatus according to the second embodiment. For convenience' sake, like reference number refers to like functional unit that functions in the same way with each unit shown in FIG. 1, and explanations thereof will be omitted.

As shown in FIG. 10, an X-ray angiography apparatus 200 includes a coronary artery analyzing unit 207, an analysis-result storage unit 208, and an analysis-image-for-synthesis creating unit 212 instead of the coronary artery analyzing unit 107, the analysis-result storage unit 108, and the analysis-image-for-synthesis creating unit 112 in the X-ray angiography apparatus 100. The X-ray angiography apparatus 200 additionally includes an analysis-result-for-synthesis selecting unit 214 and an analysis-result-for-synthesis switching unit 215.

The coronary artery analyzing unit 207 performs coronary artery analysis for a plurality of items such as a running direction of a blood vessel, a blood flow rate, plaque characteristics, and a rate of stenosis other than the angiostenosis part. The analysis-result storage unit 208 stores coronary artery analysis results for the items such as the running direction of the blood vessel, the blood flow rate, the plaque characteristics, and the rate of stenosis, other than the angiostenosis part.

The analysis-result-for-synthesis selecting unit 214 sets which item of the analysis results stored in the analysis-result storage unit 208 is to be synthesized and displayed on an X-ray angiographic image. When the analysis-result-for-synthesis selecting unit 214 sets a plurality of analysis results to be synthesized and displayed, all the set analysis results are simultaneously synthesized and displayed. Alternatively, in this setting, setting can be divided into each phase being treated, and an analysis content can be individually set, for example, an image of the running direction of the blood vessel at the time of inserting the guide wire, and an image of the angiostenosis part at the time of positioning of a treatment tool such as a stent with respect to a target to be treated.

Further, when a plurality of analysis results are superposed at the same position in the image, a priority level of superposition of the analysis results and transparent superposition are set so that information is not lost due to superposition. The setting can be changed by an operator before or during an operation.

The analysis-result-for-synthesis switching unit 215 switches the analysis image set by the analysis-result-for-synthesis selecting unit 214 with a progress of a treatment phase. The analysis image can be manually switched by the operator or can be automatically switched according to an approaching position of the catheter.

Figure 11:
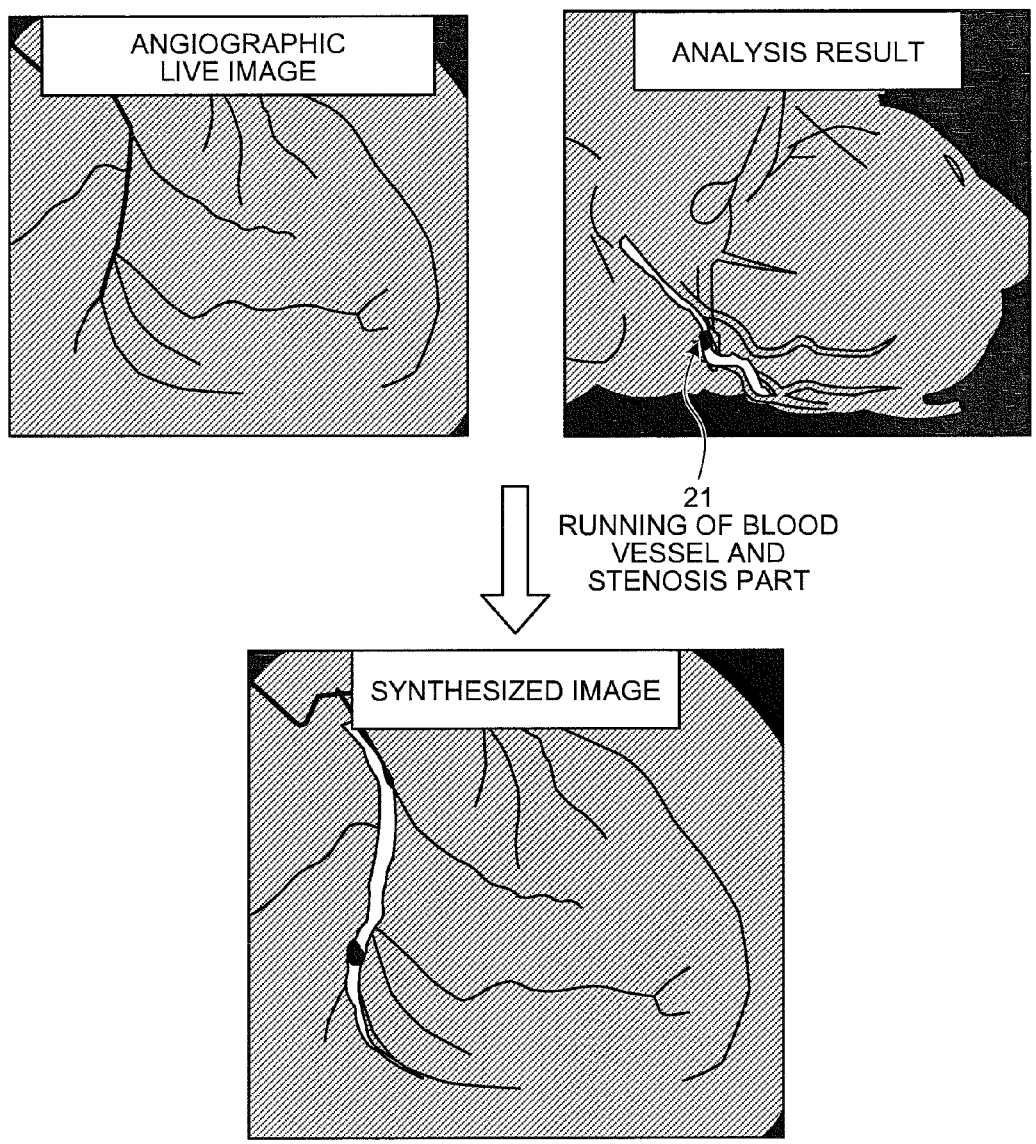
FIG. 11 is a diagram illustrating an example of a synthesized image.

The analysis-image-for-synthesis creating unit 212 creates analysis images for synthesis based on switching by the analysis-result-for-synthesis switching unit 215. FIG. 11 is a diagram illustrating an example of the synthesized image displayed by the analysis-image synthesizing and displaying unit 113. In FIG. 11, a running of a blood vessel and a stenosis part 21 are displayed superposed on an X-ray angiographic image.

In the second embodiment, the analysis-result storage unit 208 stores the coronary artery analysis results for the items analyzed by the coronary artery analyzing unit 207. The analysis-result-for-synthesis switching unit 215 switches an item to be synthesized to the item set by the analysis-result-for-synthesis selecting unit 214 among the coronary artery analysis results stored in the analysis-result storage unit 208. Accordingly, various coronary artery analysis results can be switched, synthesized, and displayed, with the progress of the treatment phase.

In the first and second embodiments, a case that one synthesized image is displayed on one display device has been explained. However, a plurality of images can be displayed on one display device or the images can be displayed on a plurality of display devices. In a third embodiment of the present invention, a case of displaying the images using a plurality of display devices is explained.

Figure 12:
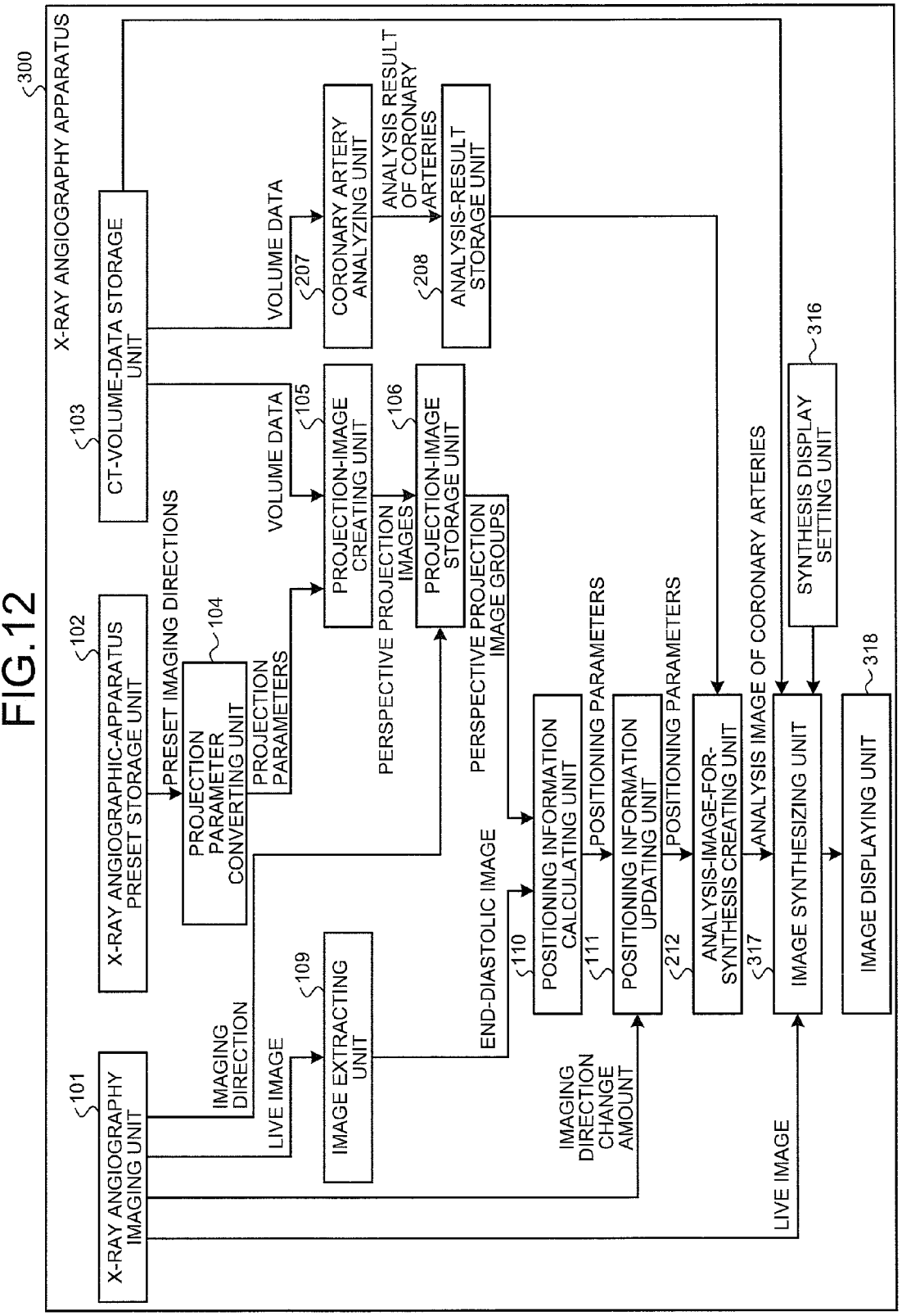
FIG. 12 is a functional block diagram of a configuration of an X-ray angiography apparatus according to a third embodiment of the present invention.

FIG. 12 is a functional block diagram of a configuration of the X-ray angiography apparatus according to the third embodiment. For convenience' sake, like reference number refers to like functional unit that functions in the same way with each unit shown in FIG. 10, and explanations thereof will be omitted.

As shown in FIG. 12, an X-ray angiography apparatus 300 includes a synthesis display setting unit 316, an image synthesizing unit 317, and an image displaying unit 318 instead of the analysis-image synthesizing and displaying unit 113 in the X-ray angiography apparatus 300.

The synthesis display setting unit 316 sets which image is displayed at which position. The setting can be changed by an operator before and during an operation. For example, as a type of the image, the synthesis display setting unit 316 sets any one of:

only an unsynthesized X-ray angiographic image;

only a synthesized image of the X-ray angiographic image and the analysis result;

two types of images, that is, the unsynthesized X-ray angiographic image and the synthesized image of the X-ray angiographic image and the analysis result;

two types of images, that is, the unsynthesized X-ray angiographic image and a synthesized image of a heart shape image of the heart area volume data and the analysis result; and two types of images, that is, the synthesized image of the X-ray angiographic image and the analysis result, and the synthesized image of the heart shape image of the heart area volume data and the analysis result.

As display positions, for example, in the case of two types of display images, the synthesis display setting unit 316 sets any one of:

display images on separate display devices;

display images in parallel on one display device; and display an image superposed on a part of the unsynthesized X-ray angiographic image.

The image synthesizing unit 317 creates a synthesized image based on the setting performed by the synthesis display setting unit 316. The image displaying unit 318 displays the X-ray angiographic image or the synthesized image based on the setting performed by the synthesis display setting unit 316.

Figure 13:
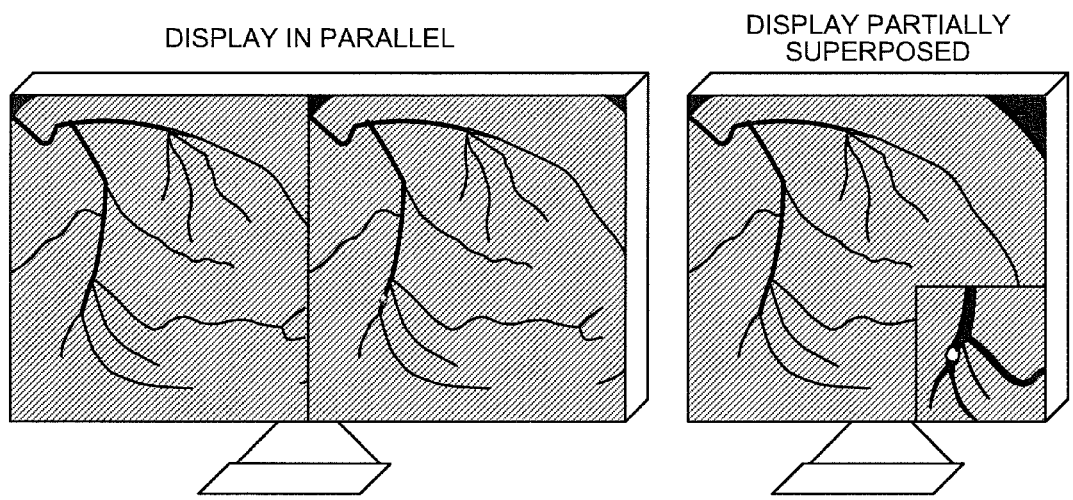
FIG. 13 is a diagram illustrating display examples of two types of images.

FIG. 13 is a diagram illustrating display examples of two types of images. In FIG. 13, a case that two types of images, that is, the unsynthesized X-ray angiographic image and the synthesized image of the X-ray angiographic image and the analysis result are displayed in parallel and a case that the synthesized image is displayed superposed on a part of the unsynthesized X-ray angiographic image are shown.

As described above, in the third embodiment, a plurality of types of images are displayed on a plurality of display devices based on the setting performed by the synthesis display setting unit 316. Therefore, the operator can appropriately position and display the images, which are considered to be useful.

In the first to third embodiments, a case that the coronary artery analysis is performed using the three-dimensional volume data has been explained; however, the coronary artery analysis can be performed using four-dimensional volume data. In a fourth embodiment of the present invention, an X-ray angiography apparatus that uses four-dimensional volume data is explained.

Figure 14:
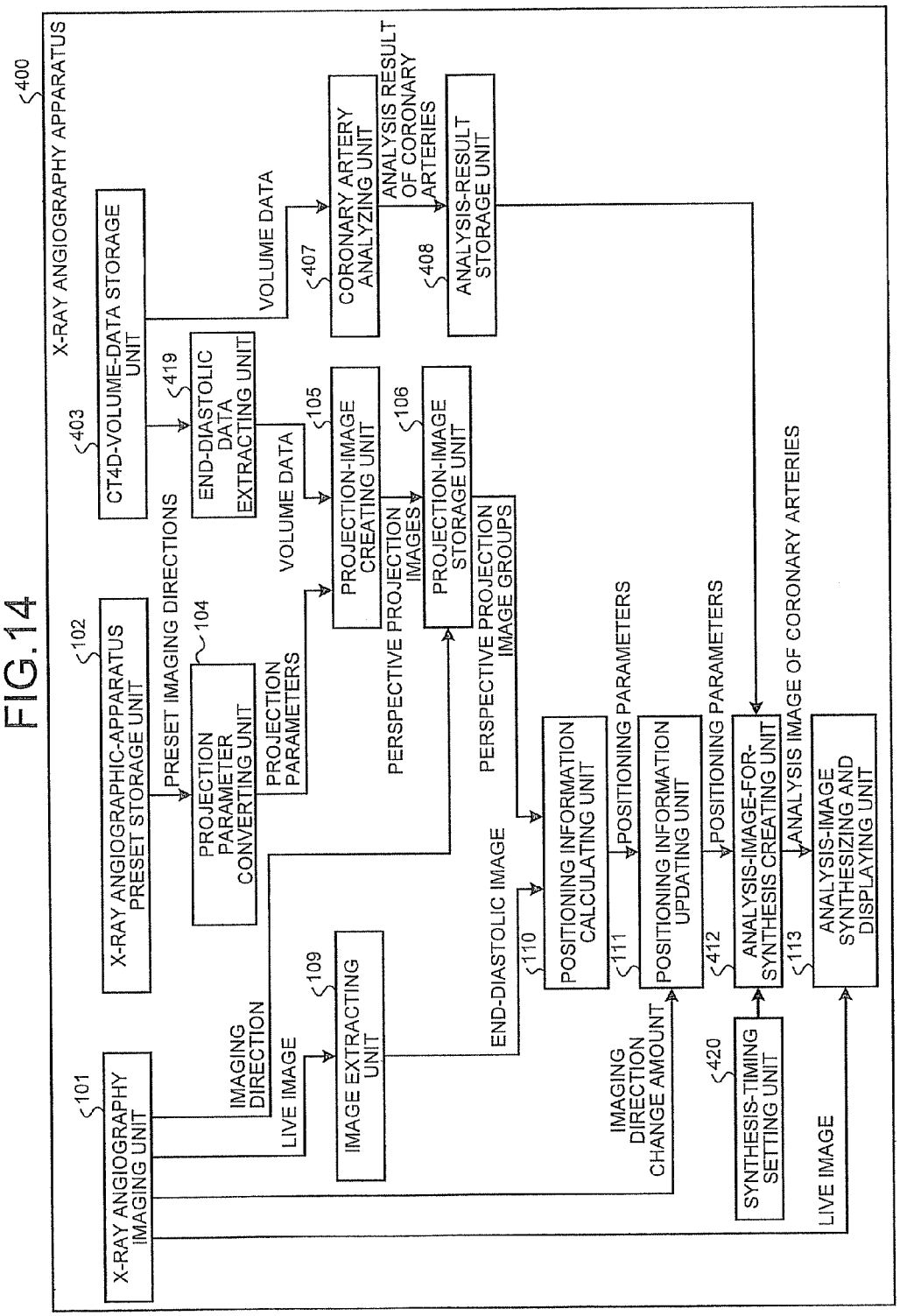
FIG. 14 is a functional block diagram of a configuration of an X-ray angiography apparatus according to a fourth embodiment of the present invention.

FIG. 14 is a functional block diagram of a configuration of the X-ray angiography apparatus according to the fourth embodiment. For convenience' sake, like reference number refers to like functional unit that functions in the same way with each unit shown in FIG. 10, and explanations thereof will be omitted.

As shown in FIG. 14, an X-ray angiography apparatus 400 includes a CT4D volume-data storage unit 403, a coronary artery analyzing unit 407, an analysis-result storage unit 408, and an analysis-image-for-synthesis creating unit 412 instead of the CT-volume-data storage unit 103, the coronary artery analyzing unit 207, the analysis-result storage unit 208, and the analysis-image-for-synthesis creating unit 212 in the X-ray angiography apparatus 200. The X-ray angiography apparatus 400 additionally includes an end-diastolic data extracting unit 419 and a synthesis-timing setting unit 420.

The CT4D volume-data storage unit 403 stores four-dimensional volume data of the heart area collected by taking images of a patient by an X-ray CT scanner. The coronary artery analyzing unit 407 performs the coronary artery analysis with respect to the four-dimensional volume data, and the analysis-result storage unit 408 stores the coronary artery analysis result performed with respect to the four-dimensional volume data. The end-diastolic data extracting unit 419 extracts end-diastolic volume data from the four-dimensional data based on electrocardiogram information registered simultaneously at the time of obtaining the four-dimensional data.

In the fourth embodiment, the data used for synthesis is four-dimensional, different from the first to third embodiments, and thus one time phase data in the data are selected to obtain the positioning parameters. Analysis images of all the time phases are created by the obtained positioning parameters. The end-diastolic volume data having relatively less heart fluctuation is used here for positioning.

The synthesis-timing setting unit 420 sets timing of a heart-beat phase for creating, synthesizing, and displaying the analysis image. The analysis image for synthesis can be created only after determining the imaging direction of the X-ray angiography apparatus 400. Therefore, a rendering load is reduced according to the following setting.

Rendering of the image is performed only for one cycle of heartbeat and repeatedly displayed.

An analysis image is not updated in the time phase of heartbeat having no (or less) fluctuation of the heart.

The synthesis display is suspended until the imaging direction is determined while the angiographic imaging direction is being changed, and creation and display of the analysis image to be synthesized is started after determination of the imaging direction.

The analysis-image-for-synthesis creating unit 412 creates the analysis image at a timing set by the synthesis-timing setting unit 420. FIG. 15 is a diagram illustrating a display example of a synthesized image. In this example, a case that the analysis image is not updated in the time phase of heartbeat having no (or less) fluctuation of the heart is shown.

As described above, in the fourth embodiment, because the analysis image is created using the four-dimensional volume data of the heart area, the analysis images can be superposed and displayed, according to a movement of the heart in the X-ray angiographic image.

In the first to fourth embodiments, a case that the analysis image is synthesized with the X-ray angiographic image of the coronary arteries and displayed has been explained. However, the present invention is not limited thereto, and is similarly applicable to a case that only an analysis image is displayed.

In the first to fourth embodiments, a case that the analysis image is synthesized with the X-ray angiographic image of the coronary arteries and displayed has been explained. However, the present invention is not limited thereto, and is similarly applicable to a case that the analysis image is synthesized with other X-ray images of a brain or the like and displayed.

In the first to fourth embodiments, a case of using the X-ray angiography apparatus has been explained. However, the present invention is not limited thereto, and is similarly applicable to other X-ray imaging apparatuses and an image processing apparatus that receives image data from the X-ray imaging apparatus, and synthesizes and displays the analysis image.

In the first to fourth embodiments, a case of using the CT volume data collected by an X-ray CT scanner has been explained. However, the present invention is not limited thereto, and is similarly applicable to a case of using the volume data collected by other medical imaging apparatuses.

In the first to fourth embodiments, a case that the projection-image creating unit 105 creates positioning images before imaging and the projection-image storage unit 106 groups and stores the positioning images for each preset has been explained. However, the present invention is not limited thereto, and is similarly applicable to a case that the positioning image is created after start of imaging. Further, the coronary artery analyzing unit 107 can be configured to detect a stenosis part after start of imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
an image obtaining unit that obtains an X-ray projection image of a subject;
a positioning-image creating unit connected to the image obtaining unit for creating positioning images with a subject center being changed within a certain range, under a condition that a point of view and a projection plane are fixed, for each of a plurality of different projection conditions using volume data collected from the subject by a medical imaging apparatus;
a projection-condition obtaining unit connected to the positioning-image creating unit for selecting an image most analogous to the X-ray projection image of the subject from the positioning images, and obtains a projection condition of the selected positioning image;
a target-region storage unit that stores volume data of a target region, among the volume data collected, as target-region volume data; and
an image display unit connected to the target-region storage unit and the projection-condition obtaining unit for creating and displaying an image of the target region based on the target-region volume data stored in the target-region storage unit and the projection condition obtained by the projection-condition obtaining unit.

2. An X-ray imaging apparatus comprising:
an imaging unit that irradiates X-rays on a subject and detects X-rays penetrating the subject to generate an X-ray projection image of the subject;
a positioning-image creating unit connected to the imaging unit for creating positioning images with a subject center being changed within a certain range, under a condition that a point of view and a projection plane are fixed, for each of a plurality of different projection conditions using volume data collected from the subject by a medical imaging apparatus;
a projection-condition obtaining unit connected to the positioning-image creating unit for selecting an image most analogous to the X-ray projection image of the subject from the positioning images, and obtains a projection condition of the selected positioning image;
a target-region storage unit that stores volume data of a target region, among the volume data collected, as target-region volume data; and
an image display unit connected to the target-region storage unit and the projection-condition obtaining unit for creating and displaying an image of the target region based on the target-region volume data stored in the target-region storage unit and the projection condition obtained by the projection-condition obtaining unit.

3. The X-ray imaging apparatus according to claim 2, further comprising a synthesized-image display unit that synthesizes an image created by the image display unit with an X-ray projection image being taken, and displays a synthesized image.

4. The X-ray imaging apparatus according to claim 3, further comprising a projection-condition updating unit that updates the projection condition corresponding to a change of an imaging condition based on the obtained projection condition, when the imaging condition of the subject is changed.

5. The X-ray imaging apparatus according to claim 4, wherein
the synthesized-image display unit can simultaneously display a plurality of types of images, and
the X-ray imaging apparatus further comprises a display setting unit that sets a plurality of types of images and display positions displayed by the synthesized-image display unit.

6. The X-ray imaging apparatus according to claim 3, wherein the positioning-image creating unit has a function of creating a plurality of positioning images beforehand for each imaging condition preset in the X-ray imaging apparatus and storing the positioning images in an image database, and the projection-condition obtaining unit has a function of selecting the positioning images corresponding to the imaging condition selected at a time of X-ray imaging of the subject from the image database.

7. The X-ray imaging apparatus according to claim 6, wherein
the synthesized-image display unit can simultaneously display a plurality of types of images, and
the X-ray imaging apparatus further comprises a display setting unit that sets a plurality of types of images and display positions displayed by the synthesized-image display unit.

8. The X-ray imaging apparatus according to claim 3, further comprising a target-region selecting unit that selects a target region to be synthesized and displayed from a plurality of target regions, wherein
the target-region storage unit stores volume data of the target regions, and
the image display unit creates and displays an image of the target region selected by the target-region selecting unit.

9. The X-ray imaging apparatus according to claim 8, wherein
the synthesized-image display unit can simultaneously display a plurality of types of images, and
the X-ray imaging apparatus further comprises a display setting unit that sets a plurality of types of images and display positions displayed by the synthesized-image display unit.

10. The X-ray imaging apparatus according to claim 2, wherein
the synthesized-image display unit can simultaneously display a plurality of types of images, and
the X-ray imaging apparatus further comprises a display setting unit that sets a plurality of types of images and display positions displayed by the synthesized-image display unit.

11. The X-ray imaging apparatus according to claim 2, further comprising a projection-condition updating unit that updates the projection condition corresponding to a change of an imaging condition based on the obtained projection condition, when the imaging condition of the subject is changed.

12. The X-ray imaging apparatus according to claim 11, wherein the positioning-image creating unit has a function of creating a plurality of positioning images beforehand for each imaging condition preset in the X-ray imaging apparatus and storing the positioning images in an image database, and
the projection-condition obtaining unit has a function of selecting the positioning images corresponding to the imaging condition selected at a time of X-ray imaging of the subject from the image database.

13. The X-ray imaging apparatus according to claim 11, further comprising a target-region selecting unit that selects a target region to be synthesized and displayed from a plurality of target regions, wherein
the target-region storage unit stores volume data of the target regions, and
the image display unit creates and displays an image of the target region selected by the target-region selecting unit.

14. The X-ray imaging apparatus according to claim 2, wherein the positioning-image creating unit has a function of creating a plurality of positioning images beforehand for each imaging condition preset in the X-ray imaging apparatus and storing the positioning images in an image database, and
the projection-condition obtaining unit has a function of selecting the positioning images corresponding to the imaging condition selected at a time of X-ray imaging of the subject from the image database.

15. The X-ray imaging apparatus according to claim 14, further comprising a target-region selecting unit that selects a target region to be synthesized and displayed from a plurality of target regions, wherein
the target-region storage unit stores volume data of the target regions, and
the image display unit creates and displays an image of the target region selected by the target-region selecting unit.

16. The X-ray imaging apparatus according to claim 2, further comprising a target-region selecting unit that selects a target region to be synthesized and displayed from a plurality of target regions, wherein
the target-region storage unit stores volume data of the target regions, and
the image display unit creates and displays an image of the target region selected by the target-region selecting unit.

17. The X-ray imaging apparatus according to claim 2, wherein
the volume data is time-series volume data,
the X-ray imaging apparatus further comprises a volume-data extracting unit that extracts one time-phase volume data from the time-series volume data, and
the positioning-image creating unit creates a plurality of positioning images based on an imaging condition of the X-ray imaging apparatus, using the volume data extracted by the volume-data extracting unit.

18. An X-ray imaging method comprising:
irradiating X-rays on a subject;
detecting X-rays penetrating the subject;
generating an X-ray projection image of the subject;
creating positioning images with a subject center being changed within a certain range, under a condition that a point of view and a projection plane are fixed, for each of a plurality of different projection conditions using volume data collected from the subject by a medical imaging apparatus;
selecting an image most analogous to the X-ray projection image of the subject from the positioning images;
obtaining a projection condition of the selected positioning image;
storing volume data of a target region, among the volume data collected, as target-region volume data; and
creating and displaying an image of the target region based on the target-region volume data and the projection condition.

* * * * *